(12) United States Patent
Chandler et al.

(10) Patent No.: US 7,292,676 B1
(45) Date of Patent: Nov. 6, 2007

(54) SYSTEM FOR PHASE-CONTRAST X-RAY RADIOGRAPHY USING X PINCH RADIATION AND A METHOD THEREOF

(75) Inventors: Katherine Chandler, Ithaca, NY (US); Tatiana Chelkovenko, Moscow (RU); David Hammer, Ithaca, NY (US); Sergei Pikuz, Moscow (RU); Daniel Sinars, Albuquerque, NM (US); Byungmoo Song, Ithaca, NY (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 91 days.

(21) Appl. No.: 11/215,200

(22) Filed: Aug. 23, 2005

Related U.S. Application Data

(63) Continuation-in-part of application No. 10/423,462, filed on Apr. 25, 2003, now abandoned.

(60) Provisional application No. 60/375,499, filed on Apr. 25, 2002.

(51) Int. Cl.
*G21G 4/00* (2006.01)

(52) U.S. Cl. .................................... 378/119; 378/122
(58) Field of Classification Search ................ 378/119, 378/122; 250/504 R
See application file for complete search history.

(56) References Cited

U.S. PATENT DOCUMENTS 5,102,776 A * 4/1992 Hammer et al. ............ 430/311

* cited by examiner

*Primary Examiner*—Jurie Yun
(74) *Attorney, Agent, or Firm*—Brian J. Lally; Michael J. Dobbs; Paul A. Gottlieb (57) ABSTRACT

A radiograph system with an anode plate, a cathode plate, and a power source coupled to said anode plate and the cathode plate. At least two wires coupled between the anode plate and the cathode plate provide a configuration to form an X-pinch having a photon source size of less than five microns at energies above 2.5 keV. Material at the configuration forming the X-pinch vaporizes upon application of a suitable current to the wires forming a dense hot plasma and emitting a single x-ray pulse with sufficient photons having energies in the range of from about 2.5 keV to about 20 keV to provide a phase contrast image of an object in the path of the photons. Multiple simultaneous images may be formed of a plurality of objects. Suitable filters and x-ray detectors are provided.

20 Claims, 13 Drawing Sheets

EXPERIMENTAL SETUP

SOURCE: 25 μm Nb X PINCH. MAGNIFICATION X93

SYSTEM FOR PHASE-CONTRAST X-RAY RADIOGRAPHY USING X PINCH RADIATION AND A METHOD THEREOF

RELATED APPLICATIONS

This application is a Continuation-In-Part Application of, and claims priority to, U.S. patent application Ser. No. 10/423,462 filed Apr. 25, 2003, which in turn claims priority to U.S. Provisional Application No. 60/375,499 filed on Apr. 25, 2002, both of which are hereby incorporated by reference in their entireties.

CONTRACTUAL ORIGIN OF THE INVENTION

The United States Government has rights in this invention pursuant to U.S. Department of Energy (DOE) Grant No. DE-FG02-98ER54496.

BACKGROUND OF THE INVENTION

X-ray point-projection radiography using an X pinch as the x-ray source appears to be a very powerful tool for studying plasma objects like exploding wires and X pinches. In such experiments, the material atomic numbers are relatively high (Z>12) and line densities (the total mass along the ray path) are large enough to see significant x-ray absorption. But in some tests, very small amounts of low Z materials, such as the residual plastic insulation around an exploded wire, have been clearly visible in images. The explanation of this phenomenon is that wave optics, rather than just the usual ray optics, must be taken into account in the radiographic image analysis. If the source of radiation is highly coherent and the film is placed far enough behind the object being radiographed, a fringe pattern is seen that results from the interference of different parts of the x-ray beam that are diffracted and refracted by sample structures. A combination of absorption, refraction and diffraction effects, involving interference fringes at the edges of sample features, will be visible on the film. The first observations of such fringe patterns with x-ray beams were made with x-ray radiation with energies of 10-50 keV from a synchrotron and with x-rays from a microfocus x-ray tube with a voltage of 40-60 keV. As is known, spatial coherence (or small effective size of the source) is much more important than spectral coherence.

X-ray radiation with energies higher than 1-20 keV is useful for imaging strongly absorbing objects, such as several cm scale or larger life forms, thick tissue samples, parts in manufacturing processes, and samples of interest in material science. In order to study small biological objects, such as insects, tissue samples from 1 mm up to a few cm, and plants up to a few cm thick, softer radiation (E=1-20 keV) is required.

The 1-20 keV spectral band is impractical to access using small, table-top size devices like x-ray tubes and laser plasmas. Microfocus x-ray tubes have very low efficiency in the wavelength band <10 keV, resulting in low radiation intensity and long exposure time. For a laser plasma to reach this spectral band, extremely high power density is required, and it is practically impossible to achieve a source size smaller than 10-15 microns without paying a large efficiency penalty by using a tiny pinhole. Synchrotrons are an excellent source of 5-20 keV radiation, but they are extremely expensive and not available everywhere.

Previous disclosures have investigated the use of X-pinch as an X-ray source for micro-lithography and other uses but have failed to teach the use of X-pinch as a source of high resolution phase contrast radiography.

For example, U.S. Pat. No. 5,102,775 issued to Hammer et al, discloses a method and apparatus for x-ray microlithography using an X-pinch having a source size of a few tens of microns, formed by the crossing of two wires constructed out of aluminum or magnesium creating a photon having an energy of up to 1.6-1.84 KeV. However, the taught wire materials, energy levels and resulting source sizes are generally insufficient for providing phase-contrast resolution less than 3 microns, and appear incapable of producing a resolution of approximately 1 micron or less as is desirable for high resolution phase contract radiography.

SUMMARY OF THE INVENTION

An important object of the present invention is to provide a system and method using an X pinch as an ideal source for x-ray phase contrast imaging in the 3-20 keV spectral band utilizing its extremely small size (about 1 micron up to 10 keV or higher) and high brightness.

A salient aspect of the invention is the ability to create and use a very small photon source size. Less than or equal to about 5 microns, preferably less than about 3 microns, and even more preferably a source size less than or equal to approximately 1 micron. An advantage of using very small sources sizes is increased edge enhancement in an image and ability to obtain resolutions on the order of less than or equal to approximately 3 microns, and even resolutions on the order of approximately 1 micron and less.

Another object of the invention is to provide a system and method of the type set forth wherein the x-ray pulse duration of the X-pinch is very short (less than 200 ps), making it useful for imaging very fast events.

Another object and advantage of the invented system and method is the ability to use multiple wires at the cross point to effectively increase the radiated energy without increasing the source size when a higher peak current pulse is used.

Another salient aspect of the invention is the use of specified wire materials at the cross-point to produce the very small source sizes at energies up to 20 keV.

Yet another object of the invention is to provide a radiograph system comprising an anode plate; a cathode plate; a power source coupled to the anode plate and the cathode plate; and at least two wires coupled between the anode plate and the cathode plate providing a configuration to form an X-pinch having a photon source size of less than five microns at energies above 2.5 keV; wherein material at the configuration forming the X-pinch vaporizes upon application of a suitable current to the wires forming a dense hot plasma and emitting a single x-ray pulse with sufficient photons having energies in the range of from about 3 keV to about 20 keV to provide a phase contrast image of an object in the path of the photons or several objects.

A final object of the invention is to provide a method providing phase contrast images of an object by subjecting the object to photons having energies in the range of from about 7 keV to about 20 keV, comprising positioning one or more objects around an X-pinch formed by at least two pairs of wires which when vaporized emit photons having energies in the range of from about 7 keV to about 20 keV from a spot source not greater than about five microns to form a single contrasted image of each object, positioned at a predetermined distance from each object to achieve refraction/diffraction enhancement of the object for a preselected photon energy range, and supplying a high current pulse to the X-pinch to vaporize the metal wires, producing a plasma, magnetically pinching the plasma to very small size and high temperature, and forming an X-ray source of photons radiating the objects.

Additional advantages, objects and novel features of the invention will become apparent to those skilled in the art upon examination of the following and by practice of the invention.

BRIEF DESCRIPTION OF THE DRAWINGS

FIG. 2b is an enlarged view of a portion of the radiograph image of the insulated 25 µm W wire shown in FIG. 2a;

FIG. 2c is a graph of the film optical density profile across the image shown in FIG. 2a;

FIG. 3a is a graph of film spectral response for radiation passed through the dense core and plastic shell from the exploded W wire shown in FIG. 2a;

FIG. 3b is an enlarged view of a portion of the graph shown in FIG. 3a;

FIG. 7a is an enlarged view of portion a.1 of the radiograph image of the house fly shown in FIG. 6a;

FIG. 7b is an enlarged view of a portion of the radiograph image of the housefly shown in FIG. 7a;

FIG. 7c is an enlarged view of another portion of the radiograph image of the house fly shown in FIG. 6a;

FIG. 7d is an enlarged view of a portion of the radiograph image of the house fly shown in FIG. 7c;

FIG. 12 shows x-ray images obtained with x-rays >8 keV, including a ~1 mm slice of marbled meat (both muscle tissue and fat), an optical image of which is also shown at the upper left. The marbling is clearly visible in the x-ray image in the radiograph obtained with 8-10 keV plus >12 keV radiation. The wire mesh in the upper portion of this radiograph indicates that this is a double image, accounting for the lack of edge-enhancement by the phase-contrast processes in the image of a 100 micron boron fiber with a 17 micron W core that is boxed in the meat radiograph. However, the same fiber was imaged in another test using the same filters (0.5 mm Mylar and 5 microns of Ta) and X pinch wires, clearly showing edge-enhancement in the middle image on the left. The image at the bottom edge of a stainless steel mesh (355 microns spacing, 80 micron wire size) shows the possibility of high-resolution x-pinch imaging for x-rays >11 keV.

DETAILED DESCRIPTION OF THE INVENTION

The X pinch is a source of radiation in the 1-20 keV x-ray band with extremely small size (~1 micron above 2.5 keV up to at least 10 keV) and short pulse duration (<1 ns, and <0.2 ns above 2.5 keV). The small source size provides high spatial coherence of the imaging x-ray beam, enabling it to be used to image low absorption, low contrast objects with excellent spatial resolution. Images with spatial resolution better than 3 microns of exploded, insulated 25 micron W wire (with <1 ns time resolution) and biological objects (a house fly and a fruit fly) are used for illustrative purposes, but are not intended to be limiting. The advantages of the X-pinch over other x-ray sources are set forth hereafter. The present invention has a number of uses, such as for imaging structure in 0.1-20 mm tissue samples in a pathology lab.

X-ray point-projection radiography using an X pinch as the x-ray source is a very powerful tool for studying plasma objects, such as exploding wires and X pinches as disclosed in T. A. Shelkovenko, D. B. Sinars, S. A. Pikuz, K. M. Chandler and D. A. Hammer, "Point-projection x-ray radiography using an X pinch as the radiation source." Rev. Sci. Instrum. 72, pp. 667-670, (2001), S. A. Pikuz, T. A. Shelkovenko, J. B. Greenly, Y. S. Dimant, D. A. Hammer, "Multiphase foamlike structure of exploding wire cores." Phys. Rev. Lett. 83, pp. 4313-4316 (1999), and D. B. Sinars, Min Hu, K. M. Chandler, T. A. Shelkovenko, S. A. Pikuz, J. B. Greenly, D. A. Hammer, and B. R. Kusse. "Experiments measuring the initial energy deposition, expansion rates and morphology of exploding wires with about 1 kA/wire." Phys. Plasmas 8, pp. 216-230 (2001) which are all herein incorporated by reference in their entirety. In such experiments, the material atomic numbers are relatively high (Z>12) and line densities (the total mass along the ray path) are large enough to see significant x-ray absorption. But in some tests, very small amounts of low Z materials, such as the residual plastic insulation around an exploded wire, have been clearly visible in images as disclosed in D. B. Sinars, Min Hu, K. M. Chandler, T. A. Shelkovenko, S. A. Pikuz, J. B. Greenly, D. A. Hammer, and B. R. Kusse. "Experiments measuring the initial energy deposition, expansion rates and morphology of exploding wires with about 1 kA/wire." Phys. Plasmas 8, pp. 216-230 (2001).

The explanation of the phenomenon is that wave optics, rather than just the usual ray optics, must be taken into account in the radiographic image analysis. If the source of radiation is highly coherent and the film is placed far enough behind the object being radiographed, a fringe pattern is seen that results from the interference of different parts of the x-ray beam that are diffracted and refracted by sample structure. A combination of imaging (absorption and refraction) and diffraction effects, involving interference fringes at the edges of sample features, will be visible on the film. The first observations of such fringe patterns with x-ray beams were made with x-ray radiation with energies of 10-50 keV from a synchrotron as disclosed in A. Snigirev. I. Snigireva, V. Koch, S. Kuznetsov and Schelokov, "On the possibilities of x-ray phase contrast microimaging by coherent high-energy synchrotron radiation." Rev. Sci. Instrum. 66, pp. 5486-5492 (1995) which is herein incorporated by reference in its entirety and with x-rays from a microfocus x-ray tube with a voltage of 40-60 keV as disclosed in S. W. Wilkins, T. E. Gureyev, D. Gao, A. Pogany and A. W. Stevenson, "Phase-contrast imaging using polychromatic hard x-rays." Nature 384, pp. 335-338 (1996) which is herein incorporated by reference in its entirety. As discussed in G. Margaritondo, G. G. Tromba, "Coherence-based edge diffraction sharpening of x-ray images: a simple model." J. Appl. Phys. 85, pp. 3406-3408 (1999) which is herein incorporated by reference in its entirety, spatial coherence (or small size of the source) is much more important than spectral coherence.

The X pinch is an ideal source for x-ray phase contrast imaging in the 3-10 keV spectral band because of its extremely small size (less than 1 micron) and high brightness. Also, the x-ray pulse duration of the X-pinch is very short (less than 200 ps), and so it can be used for imaging very fast events. The XP pulser (450 kA, 100 nanosecond pulse width) used in the experiments discussed herein is described in detail in S. A. Pikuz, T. A. Shelkovenko, A. R. Mingaleev, D. A. Hammer and H. P. Neves, "Density measurements in exploding wire-initiated plasmas using tungsten wires." Phys. Plasmas 6, pp. 4272-4283 (1999) which is herein incorporated by reference in its entirety. With some wire materials and higher current than from the XP pulser, the very small source size extends to as high as 20 keV x-ray energy.

Figure 1A:
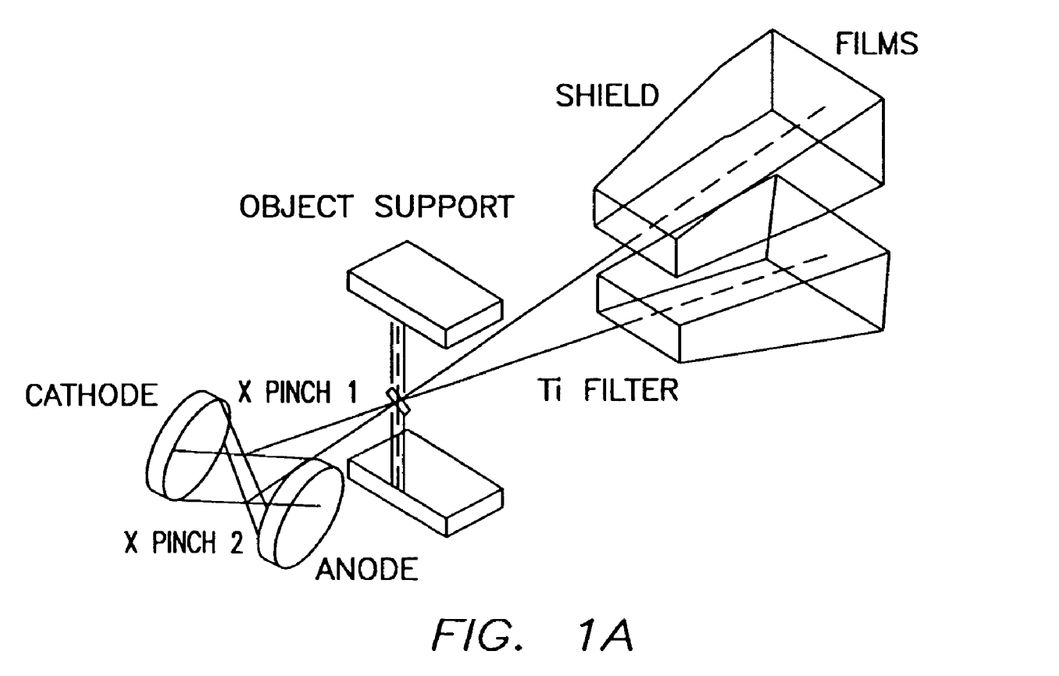
FIG. 1a is a block diagram of a system for phase-contrast x-ray radiography of low absorption materials using X pinch radiation in accordance with one embodiment of the present invention.
Figure 1B:
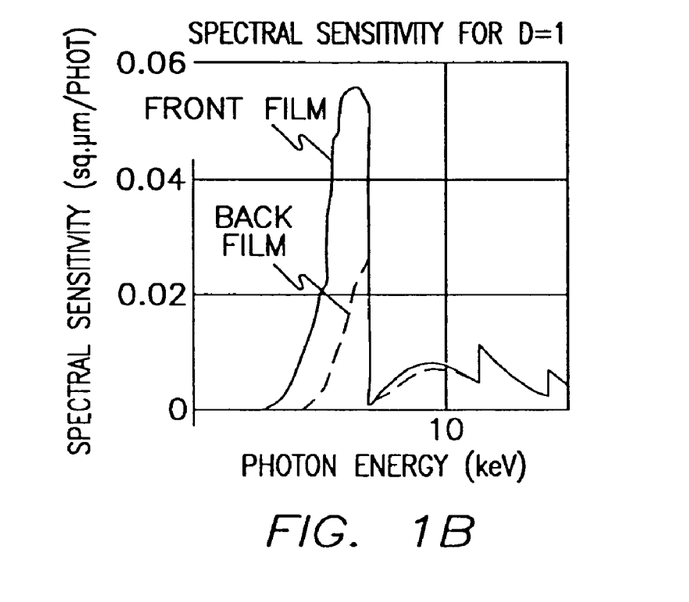
FIG. 1b is a graph of the spectral sensitivity of front and back films taking into account a 12.5 µm Ti filter.

The arrangement used to obtain radiographs is shown schematically in FIG. 1a. X-ray radiation was generated at the cross point of two thin wires placed in the cathode-anode gap of the vacuum diode of the high current (about 450 kA peak) XP pulser. Usually two X pinches were mounted in the diode in order to obtain two images of the object of interest at different times or simultaneously with different viewing angles. Images were recorded on films placed in the shields (see FIG. 1a) and protected from visible light by a 12.5 µm Ti filter. Usually, a stack of two films (Kodak Technical Pan) was used in experiments. In that case, the front film served as an additional filter for x-ray radiation reaching the second film. (There is no data for the sensitivity of Kodak Technical Pan in the x-ray spectral band, but we assumed it to be similar to the known film, Kodak RAR2497. These films are of the same type and are intended for similar applications in the optical band.) The spectral sensitivities of front and back films combined with the absorption by the Ti filter are presented in FIG. 1b.

Figure 2A:
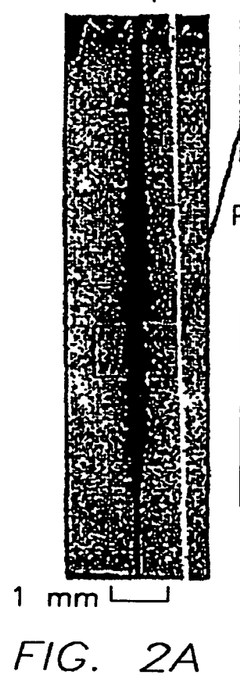
FIG. 2a is a radiograph image of an insulated 25 microns W wire after its current-driven explosion.
Figure 2B:
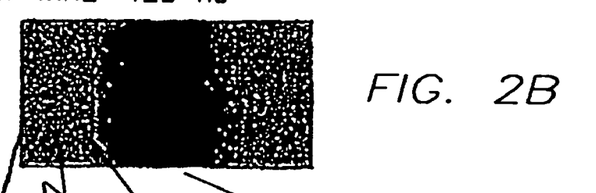
Figure 2C:
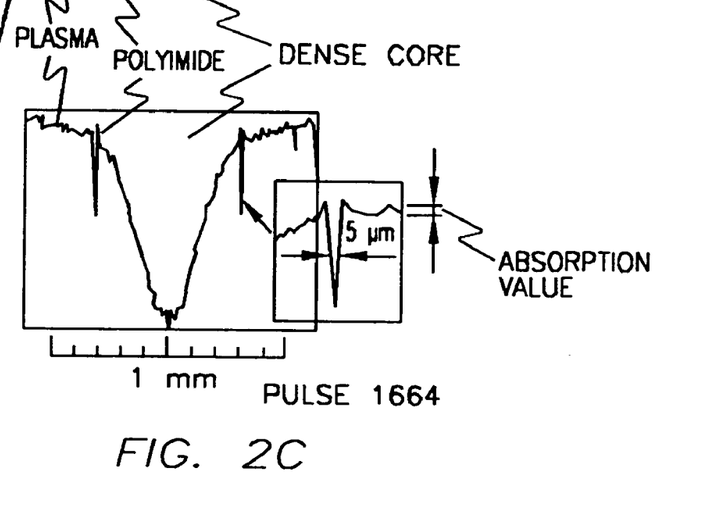
Figure 2D:
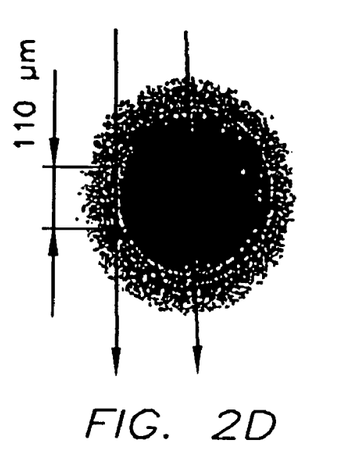
FIG. 2d is a diagram illustrating ray propagation.
Figure 3A:
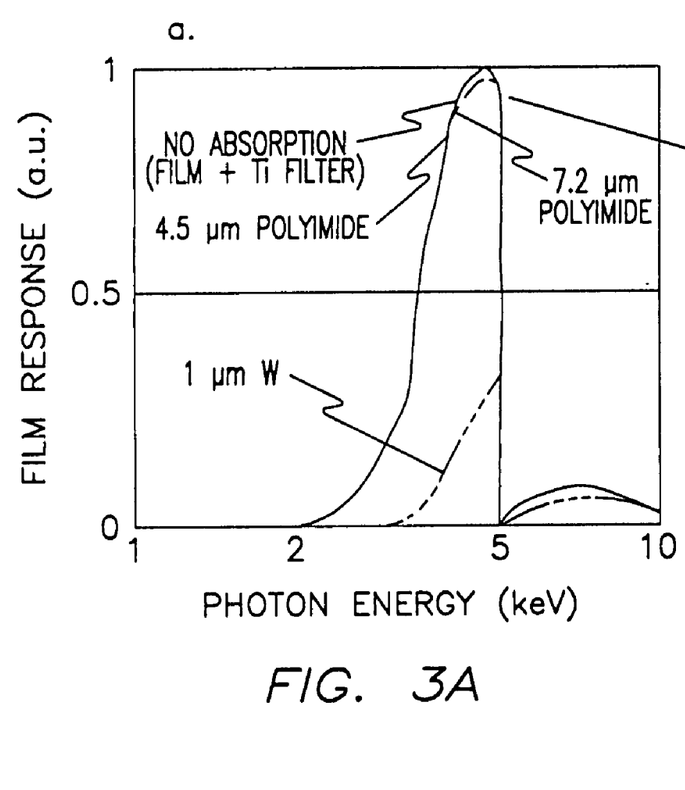
Figure 3B:
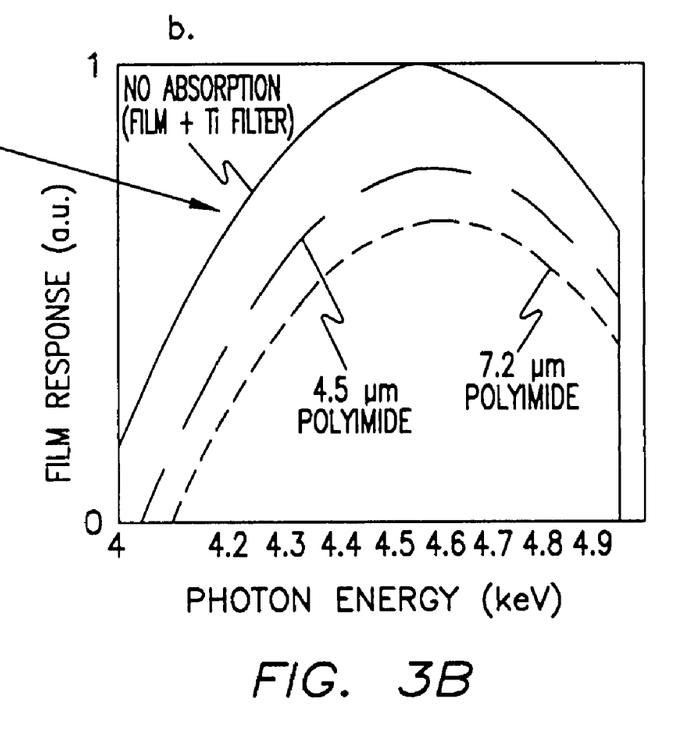

In previous experiments, some images showed very fine features resulting from some low-absorption materials. For example, FIG. 2a shows an image of an exploded 25 µm W wire under conditions described by D. B. Sinars, Min Hu, K. M. Chandler, T. A. Shelkovenko, S. A. Pikuz, J. B. Greenly, D. A. Hammer, and B. R. Kusse "Experiments measuring the initial energy deposition, expansion rates and morphology of exploding wires with about 1 kA/wire." Phys. Plasmas 8, pp. 216-230 (2001). The original wire had a 5 µm thick polyimide insulation layer, and the image (FIG. 2b) clearly shows a very thin shell surrounding the exploded wire dense core. It looks like a balloon filled with gas, see FIGS. 2c and 2d. The thickness of the shell does not exceed 5 microns. The spatial resolution in the experimental geometry, limited by diffraction, is 2-3 µm; the actual thickness of the plastic shell is probably not smaller. Assuming the whole plastic mass remained in the shell, it is easy to estimate the absorption of 3-5 keV x-rays and the expected image contrast. The absorption length of the shell is given by $L=2.83 (r\Delta r)^{1/2}$, where r is the shell radius and $\Delta r$ is the shell thickness. The material density is given by $\rho_0 = \rho_0 r_0 \Delta r_0 / r \Delta r$ where values with index 0 correspond to the initial state of the insulation shell. The equivalent absorption length (thickness of material at solid density equivalent in absorption to the material under the actual experimental conditions) in $L = L_1$ is inversely proportional to the square root of the shell thickness $L_1 = 2.83 r_0 \Delta r_0 (r \Delta r)^{-1/2}$. For wire core density measurements, the step wedge technique described in S. A. Pikuz, T. A. Shelkovenko, A. R. Mingaleev, D. A. Hammer and H. P. Neves, "Density measurements in exploding wire-initiated plasmas using tungsten wires." Phys. Plasmas 6, pp. 4272-4283 (1999) has been used. The equivalent thickness of wire material at solid density to the wire material in the core center is about 1 µm of W. Absorption curves for 1 µm W layer (center of the core) and polyimide layers with thicknesses 4.5 µm and 7.2 µm (5 µm and 2 µm shell thicknesses) calculated for a Planckian spectrum of radiation are presented in FIGS. 3a and 3b. It is obvious that the contrast of the shell image should not exceed 5-7%, but in experiments, the contrast reaches 30-40%. That can be explained using wave optics.

Figure 4A:
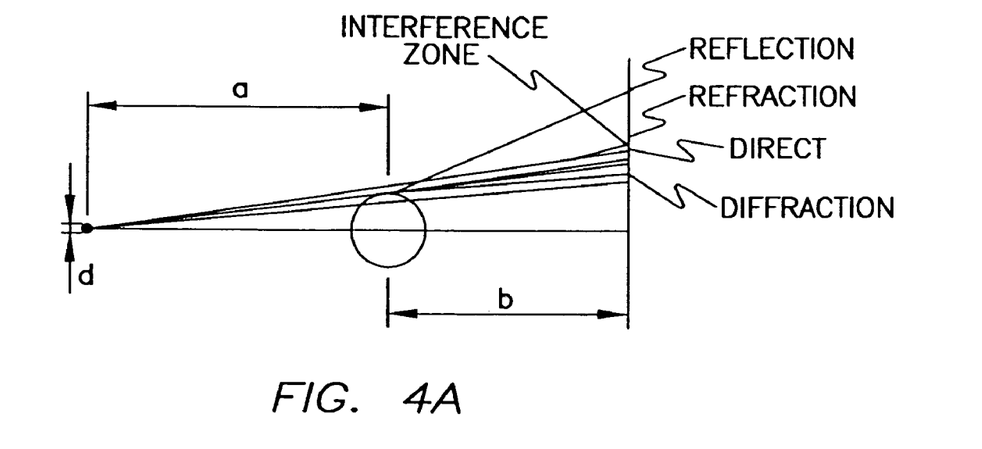
FIG. 4a is a diagram illustrating X-ray propagation through a cylindrical object.

In the general case, the full wave equations should be used, but to simplify the situation, three processes are considered: diffraction, refraction and reflection of x-rays by the object being radiographed (see FIG. 4a). For highly absorbing materials, such as W, refraction is probably not important except for a thin layer near the surface for less than 10 keV x-rays because the absorption of these x-rays is so strong. Reflection is important for the lower energy part of the spectral band mentioned above (E=2-4 keV) and requires extremely smooth reflecting surfaces. Diffraction should be important in any case. Because of the negative value of the refractive index for x-rays, there are areas in the observation plane where the direct and refracted beams overlap. If the radiation is coherent, an interference pattern should appear.

Figure 4B:
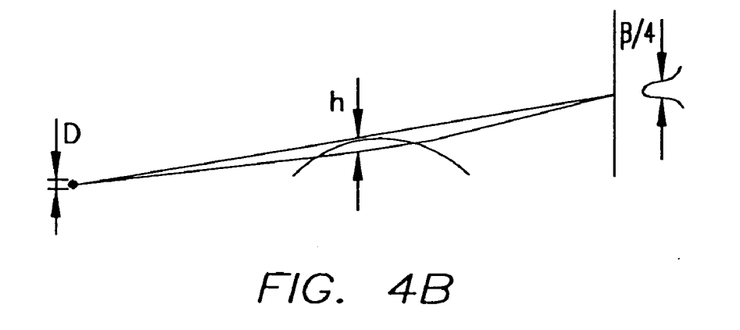
FIG. 4b is a diagram illustrating interference between direct and refracted rays.
Figure 5A:
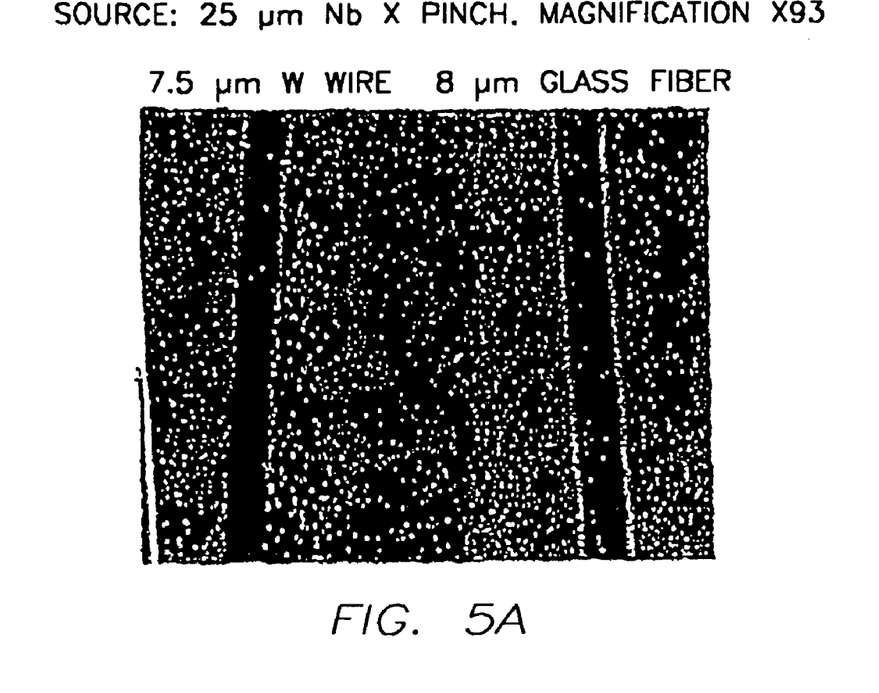
FIG. 5a is a radiograph image of a 7.5 µm W wire and an 8 µm glass fiber with magnification ×93.
Figure 5B:
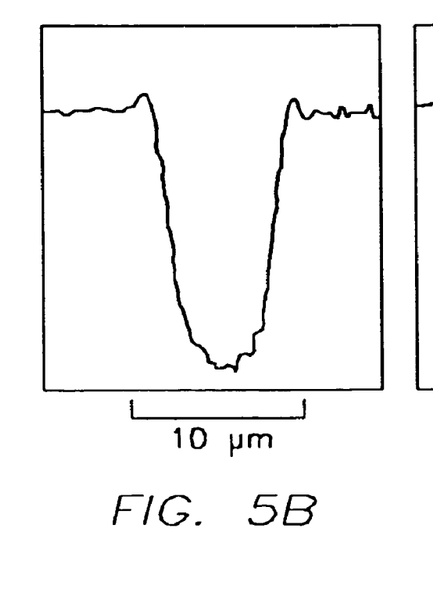
FIG. 5b is a graph of lineout through the W wire image showing little indication of refraction and diffraction of the x-rays, but perhaps some grazing-incidence reflection.
Figure 5C:
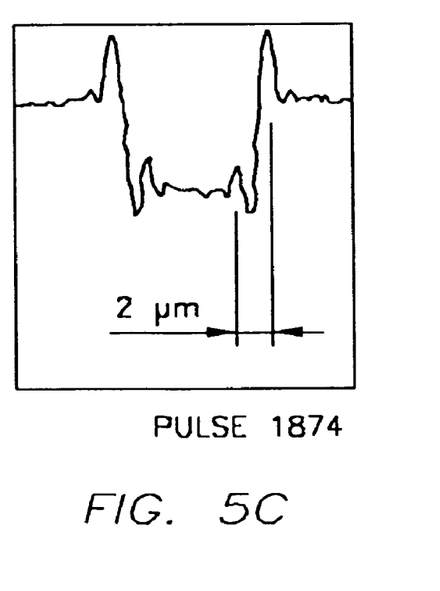
FIG. 5c is a graph of lineout through the glass fiber image showing indications of refraction, diffraction and interference.

Test images of two different objects of the same size but with different absorption are shown in FIGS. 5a-c, with the geometric magnification in the test being 93:1. (The distance from the source to the objects was 9 mm, and from the object to the film was about 1 m.) The tungsten wire (see FIGS. 5a and b) shows a rather smooth image, with little variation of intensity at the wire edge. The intensity distribution roughly corresponds to the L distribution across a solid cylindrical wire. The diffraction limit of resolution is about 1.5-1.7 µm in this geometry, but the diffraction pattern was probably smoothed by the large absorption gradient near the edge of the wire. In the image of the partially transmitting glass fiber in FIGS. 5a and c, substantial variation of the intensity is observed. This variation can be explained as the interference of direct radiation and radiation refracted away from the axis of the fiber, as illustrated in FIG. 4b.

The fringe width $\beta=\lambda b/h$ (see FIG. 4), where $\lambda$ is the x-ray wavelength, is approximately 200 µm on the film, corresponding to h=1.5 µm. In order to observe interference, the source must be small enough to satisfy $Dh/a<\lambda/2$. In our case, taking $\lambda$=3 Å, the source size must be smaller than 1 µm, a value which is consistent with other results. For practical applications, it was shown in S. W. Wilkins, T. E. Gureyev, D. Gao, A. Pogany and A. W. Stevenson, "Phase-contrast imaging using polychromatic hard X-rays." Nature 384, pp. 335-338 (1996) that a small source size is the main requirement for image enhancement from sharp material gradients. The X pinch is, therefore, a very promising source for taking advantage of this phenomenon, called phase-contrast x-ray radiography, with low contrast, weakly absorbing objects, such as biological tissue. However, a full analysis of the images requires a complete solution of the wave equation for the whole system, including all phenomena, because the diffraction limit, the source size, and fringe widths are all of the same order.

Figure 6A:
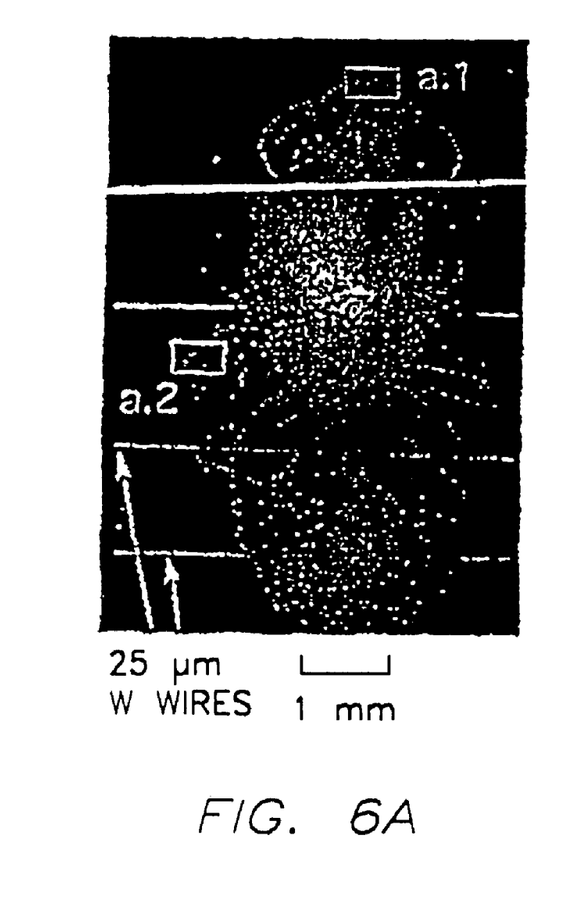
FIG. 6a is a radiograph image of a house fly.
Figure 6B:
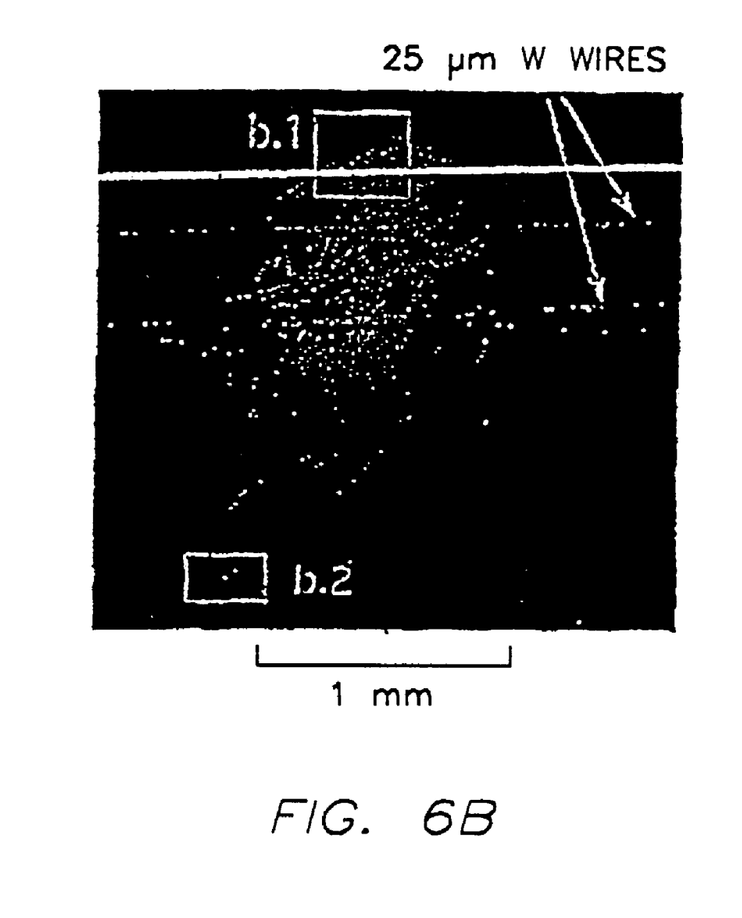
FIG. 6b is a radiograph image of a fruit fly.
Figures 7A, 7B, 7D:
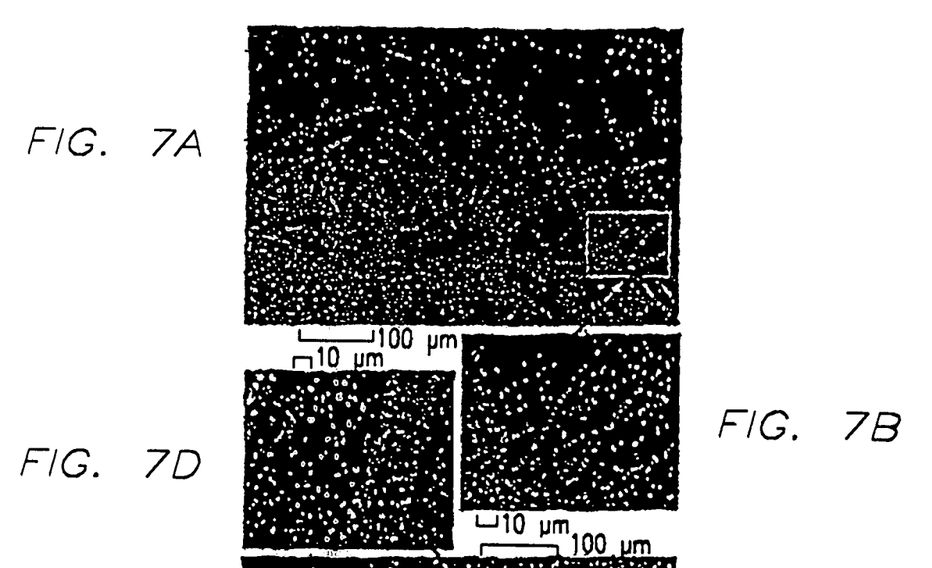
Figure 7C:
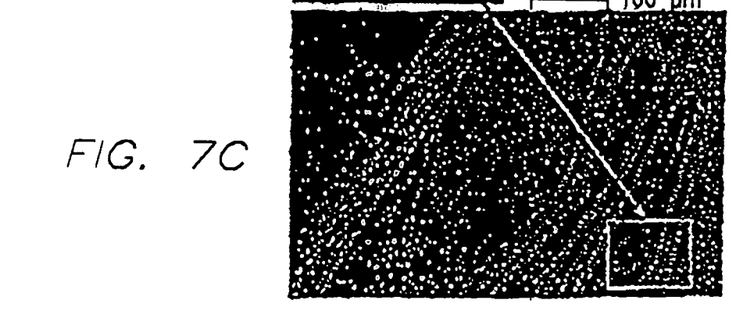
Figure 8A:
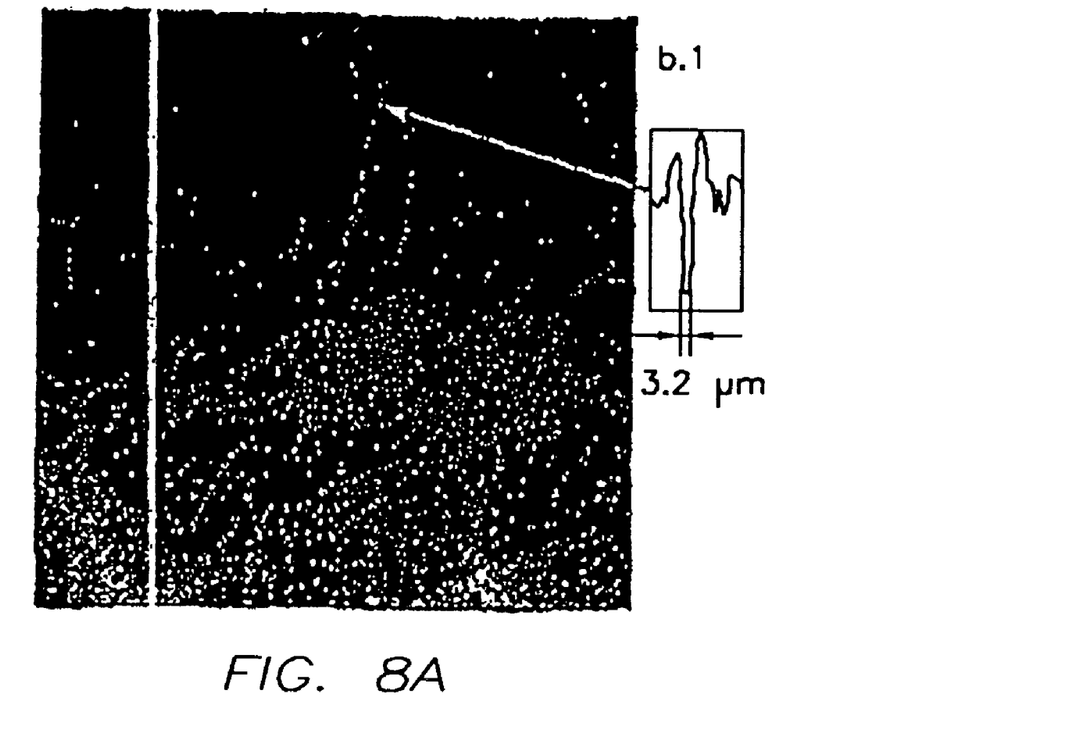
FIG. 8a is an enlarged view of a portion b.1 of the radiograph image of the fruit fly shown in FIG. 6b.
Figure 8B:
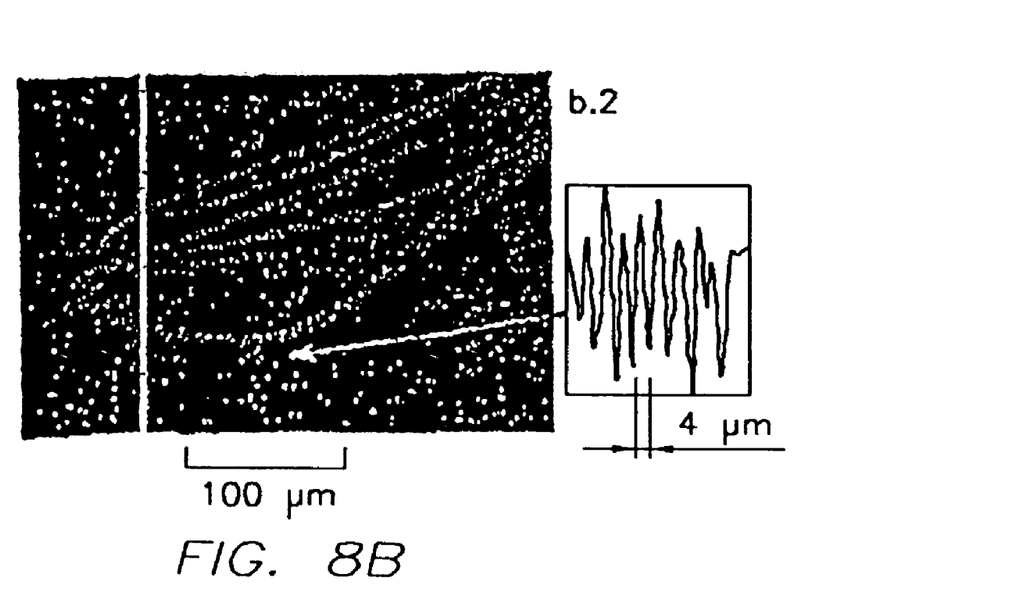
FIG. 8b is an enlarged view of portion b.2 of the radiograph image of the fruit fly shown in FIG. 6b.

To demonstrate phase contrast imaging, images of a common house fly (*Muska Domestica*) and a fruit fly (FIGS. 6a and 6b) with geometric magnifications ranging from 5:1 to 7.5:1 were taken. In the enlarged portions of the images (FIGS. 7a.1, a.2, b.1 and b.2 and 8b.1 and b.2), features smaller than 3 µm are clearly visible even on fly wings, demonstrating the extremely high sensitivity of the phase-contrast method. If absorption only is taken into account, the contrast ratio would be less than 1-2%, and these fine features would be practically invisible.

FIGS. 6 to 8 and all subparts thereof clearly show that the X pinch is a new source for phase-contrast x-ray radiography of weakly absorbing objects with micron scale features.

Figures 9A, 9B:
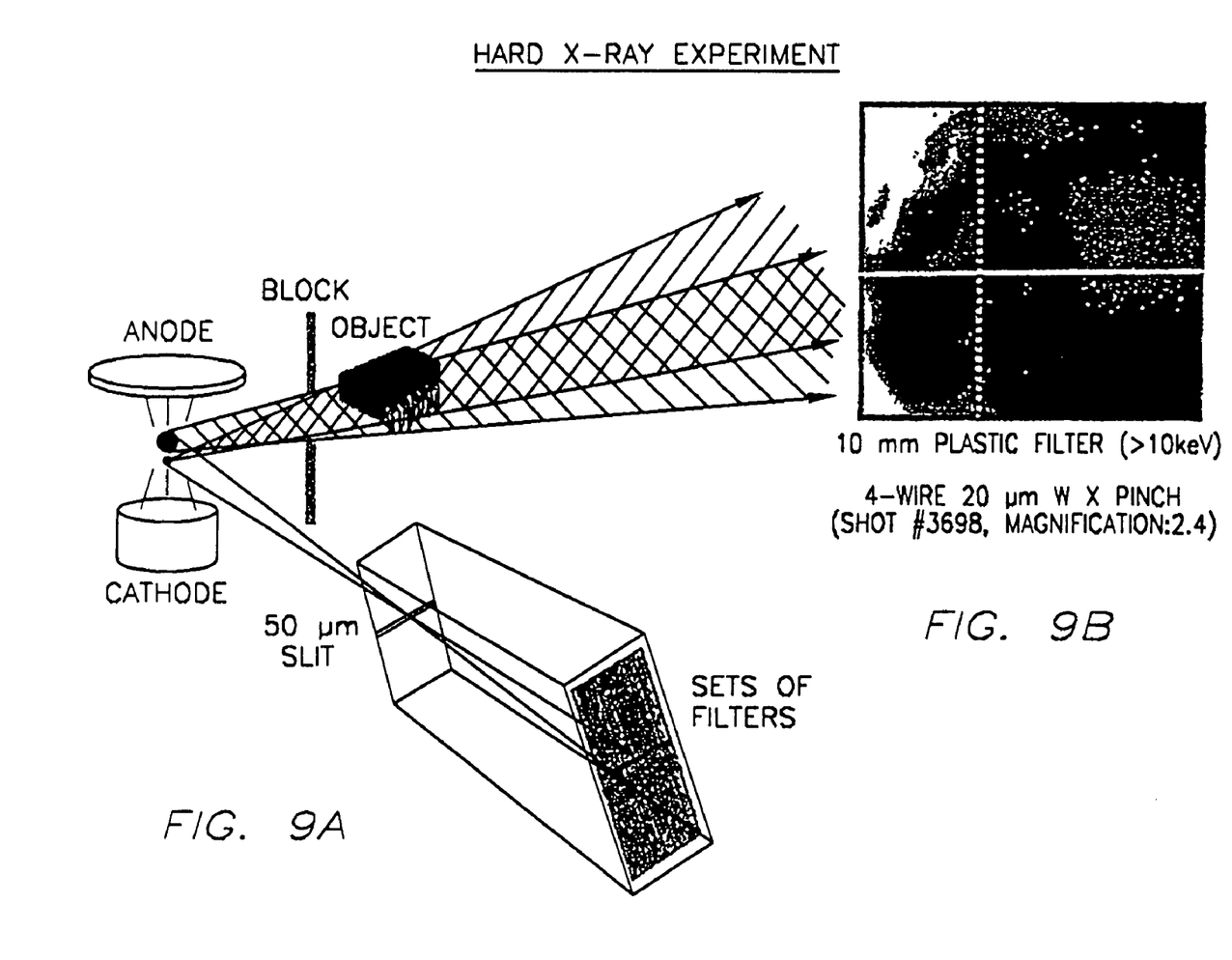
FIG. 9a is a view like FIG. 1a of another embodiment of the invention showing the possibility of multiple x-ray paths and targets.
FIG. 9b is a portion of a radiographic image made with photons >10 keV showing an electronic chip (2-3 mm thick) that was irradiated by two bright spots from one X pinch. The portion of the image that is sharp is a result of being made by a small x-ray source only; the remaining part of the image is blurred by a larger source spot of x-rays.

Referring now to FIGS. 9a and 9b, there is disclosed an experimental set-up for practicing the present invention in which an X pinch is configured by an anode and a cathode having two or more wires crossed to form the configuration resulting in the X pinch.

Up to about ten wires may be used and the X pinch is established by providing a large current pulse across the anode and cathode, resulting in a hot dense plasma emitting a single x-ray pulse.

The photons emitted by the pulse are studied for source size and energy spectrum b passing through a slit as indicated and by means of a variety of filters a selected energy range impinges the target. The energy range of photons reaching the object may be limited, for example to an energy predominantly within ±2 keV, in the range of from energies of from 1 to 20 keV. Objects useful in the radiographic system of the present invention may vary, as for example, tissue of warm bloodied animals or wires encased in a synthetic organic resin. FIG. 9b shows a portion of a radiographic image taken using a 4-wire 20 micron tungsten X pinch and a 10 mm plastic filter, the x-ray energies used for imaging thereby being greater than 10 keV.

Obtaining Small Source Size

One of salient aspects of the invention is the ability to form a source size of less than 5 microns, even source sizes on the order of about one micron or less. The ability to obtain small source size is critical because source size is directly linked with enhanced image resolution. Several factors are important to creating very small source sizes including but not limited to: the materials of the wires being crossed to form the X-pinch, the energy range (e.g., >10 KeV), and matching the wire mass to the current pulse amplitude and shape.

A variety of wires may be used to form an X pinch, including but not limited to metals like W, Nb, Mo, Ti, Ni, Cr, Pd, Mg, Al and/or alloys thereof.

However, it has been found that it is preferable to employ relatively high Z-materials including but not limited to: W, Nb, Mo, Ni and metal alloys thereof. The preferred materials can create source sizes less than 5 microns and even less than about 1 micron at energies between 2.5 and 20 keV. The mid- and high-Z materials are better than metals like Al and Mg because they radiate more intensely because they are higher Z. Titanium is not as good because the line radiation it emits near 5 keV tends to come from a larger spot (about 15 microns). Furthermore, the lower Z wire materials expand faster than the mid- and high-Z materials, which probably explains why they do not pinch to as small a spot.

As noted earlier a multitude of wires can be used crossed at to form the X-pinch. The ability to use multiple wires successfully is important to effectively utilizing higher current pulsed power machines to obtain higher intensity radiation in 1-5 micron size spots. This is because the pinch time, T, peak current, I, and wire total mass per unit length, M, obey the relationship that M is proportional to $I^2T$ (I-squared times T). (Note that the wire mass per unit length is proportional to the square of the wire radius for a given material.) Since pulse times vary only by a factor of 2 or so while current-squared can vary by a factor 25 or even much more, many wires may be needed to obtain a pinch near peak current. Thus, for the shorter pulses, for example a rise time to peak current of 50 ns, and lower peak currents, for example 50 kA, the lightest possible W wires should be used (e.g., 2 4 micron wires), while for a 500 kA generator with a 100 ns rise time to peak, the optimum mass per unit length will be about 200 times greater, requiring about 8-12 25 micron W wires.

Experimentally, we observe that the higher the energy band we choose for imaging (e.g., photon energy greater than 8 keV instead of 2.5 keV), the smaller is the x-ray source size, although above 8 keV, the change appears to be very slow. We believe this because the smallest, hottest portion of the pinch plasma disassembles the fastest, cooling in the process.

From the results of the X pinch bright spot radiation and radiographs obtained on many generators, including summarizing our own experimental results over many years on different generators we can conclude the following: to obtain a bright source of radiation, a high energy density micropinch with ~1 µm or sub µm scale size and a sub-ns x-ray pulse duration, the generator must have rate of change of current with time of at least 1 kiloampere per nanosecond, dI/dt>1 kA/ns, and the bigger this parameter is, the more intense and smaller the source can be. Proper load mass using the relationship between current, pulse rise time and mass per unit length, above, for the specific pulse parameters is an important to generate one bright point source. That is to assure maximum intensity by having the pinch (and radiation pulse) occur near, but shortly before, peak current. The latter condition assures that the current is still rising, but the rate of increase is relatively slow, because the slower rate of rise improves the probability of a singe intense, micron-scale x-ray source. Any subsequent x-ray bursts, if this prescription is followed, tend to be substantially lower photon energy (for example less than 2.5 keV), and can easily be filtered out for imaging of objects.

In practice, that probably means that for any given current pulse, the wire mass needs to be chosen to give the first emission burst perhaps 80-90% of the time from the start of the current pulse to the peak.

For example, if it is desired to image a finger and 15 keV radiation is needed to do it, if the first burst reaches 15 keV and has enough x-ray yield (joules) to make an image in that radiation, many bursts with photon energy in the 1-5 keV range can follow because we can filter out those photons anyway with a relatively thick copper (or some other) filter.

Figure 10A:
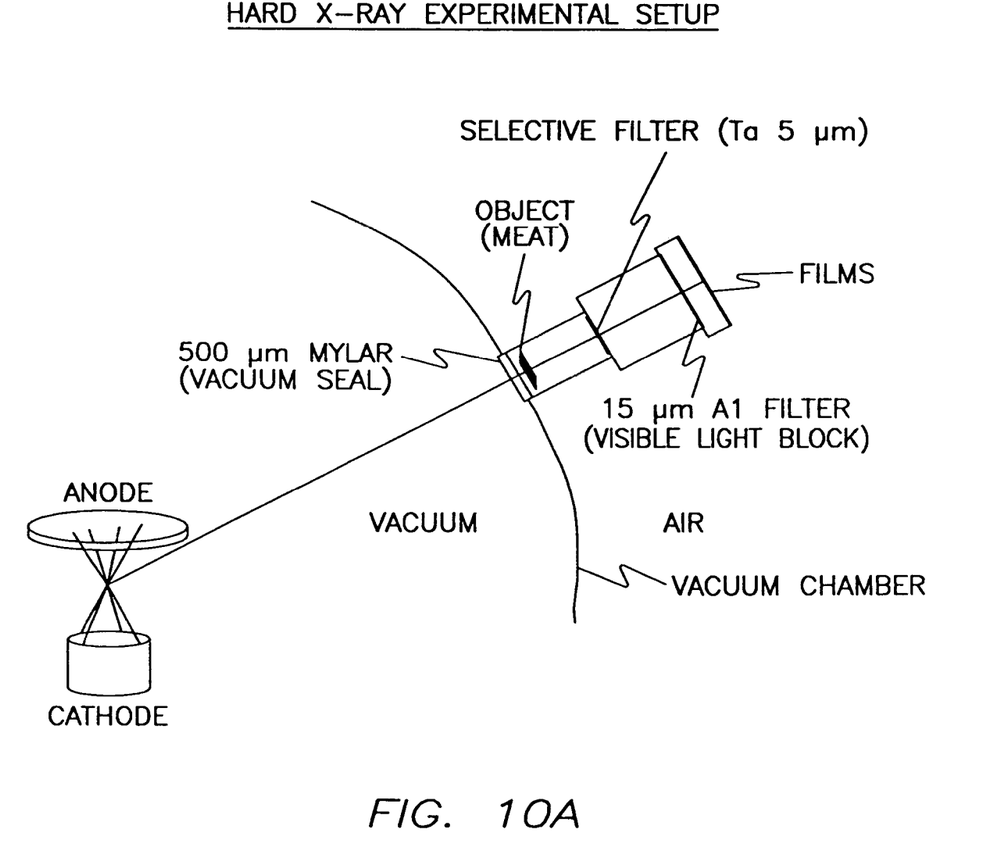
FIG. 10a is a schematic diagram for phase-contrast x-ray radiography using >7 keV x-rays similar to FIG. 1a with additional details; the object is shown in air outside the experiment chamber.

FIG. 10a shows an experimental set-ups in which the object being imaged can be outside the vacuum chamber in which the X pinch is located.

Figure 10B:
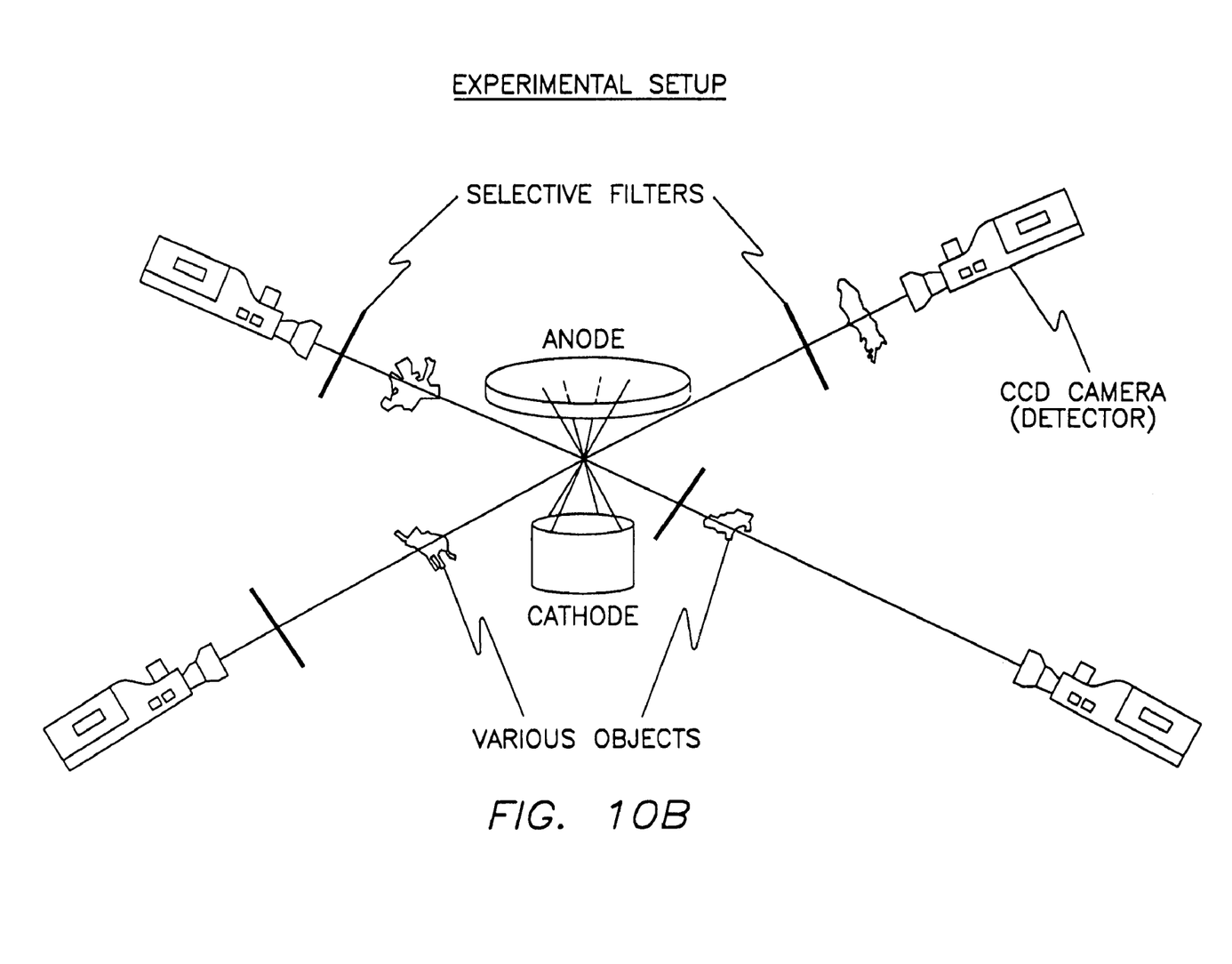
FIG. 10b is a schematic diagram like FIG. 10a with additional targets and CCD cameras to record the images in place of film.

FIG. 10b shows four different experiments set-ups in which CCD cameras are positioned to record an x-ray pulse from a X pinch for a variety of objects placed in three dimension around the X pinch. As illustrated in FIG. 10b, it is not necessary that all objects be irradiated with the same energy level of x-rays nor is it required that all objects be the same since the burst of x-ray energy from the X pinch radiates in three dimensions from the X pinch. A wide variety of objects may be simultaneously radiated to provide phase contrast images of a large number of objects.

Figure 11:
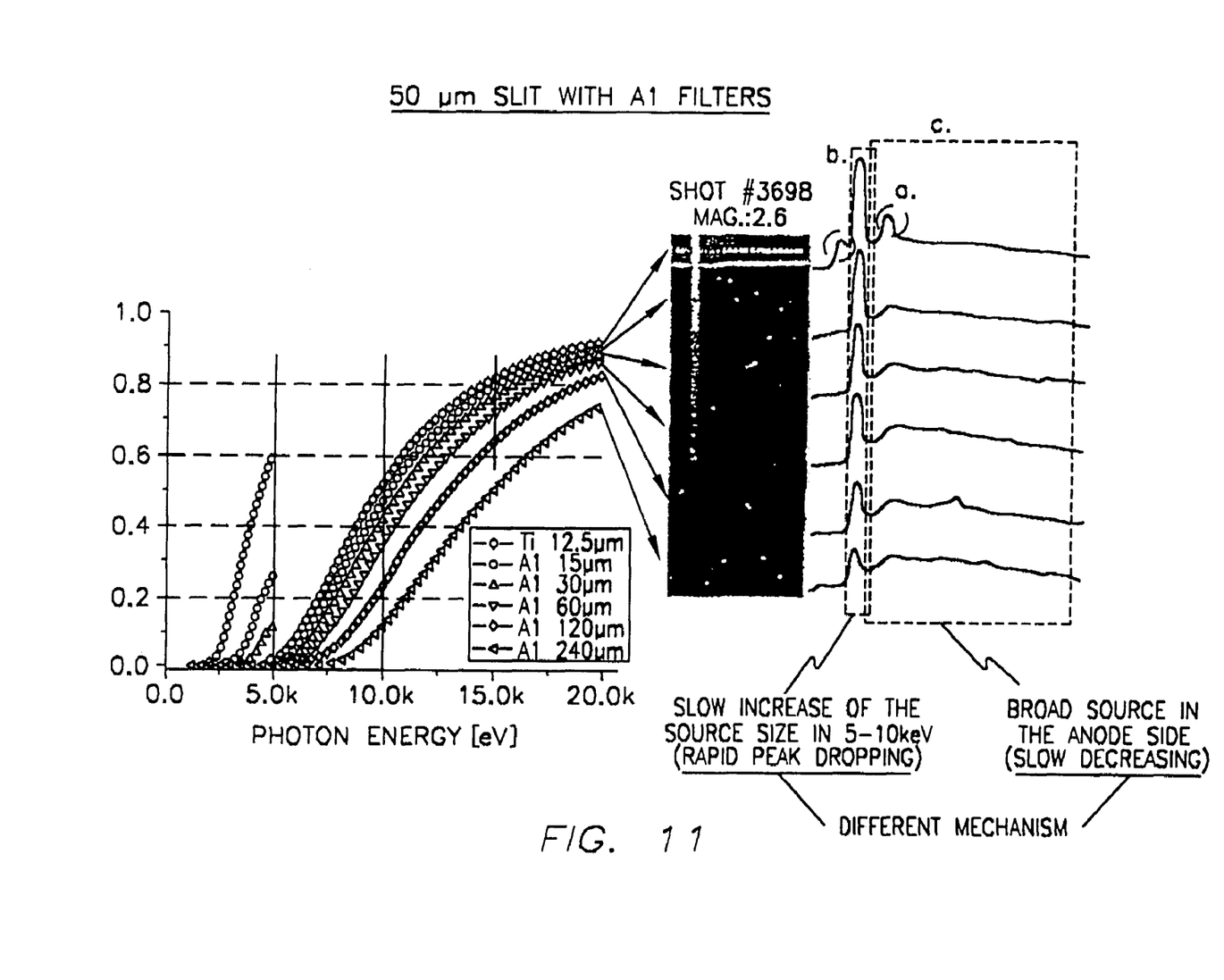
FIG. 11 shows an image of a 50 micron slit through a variety of filters that shows the relationship between source size, intensity and x-ray energy band. The filter transmission for different thickness Al filters plus 12.5 microns of Ti is shown to the left. The slit image radiograph through the different filters is shown in the center, and the lineouts through the slit image obtained through each filter are shown to the right. A small thermal source dominated by x-ray energies between 6 and 10 keV and a displaced larger x-ray source with x-rays >10 keV is indicated.

A variety of filters may be used, as is well known in the art, for instance, filters made from Ti, Al, Be, and Ta have been used previously and are known. FIG. 11 shows the result of testing the spectral content of X pinch radiation using a 50 µm slit with different Al filters in addition to a 12.5 µm Ti filter. The graph of transmission vs photon energy shows how the transmitted x-ray photon energy band increases as the Al thickness is increased. The radiograph in the center shows the image of the 50 µm slit through the various thicknesses of Al from the central bright spot of the X pinch. Notice that there is a clear image of the slit from the small X pinch source even with the thickest Al filter (photon energy above 10 keV), and that the film optical density tracings to the right of the radiograph show that sharp images of the slit are obtained even with the highest pass band. However, there is also electron beam-generated radiation that comes from the anode side of the X pinch that passes through the slit and exposes the film to the right of the exposure due to the central bright spot.

Figure 12:
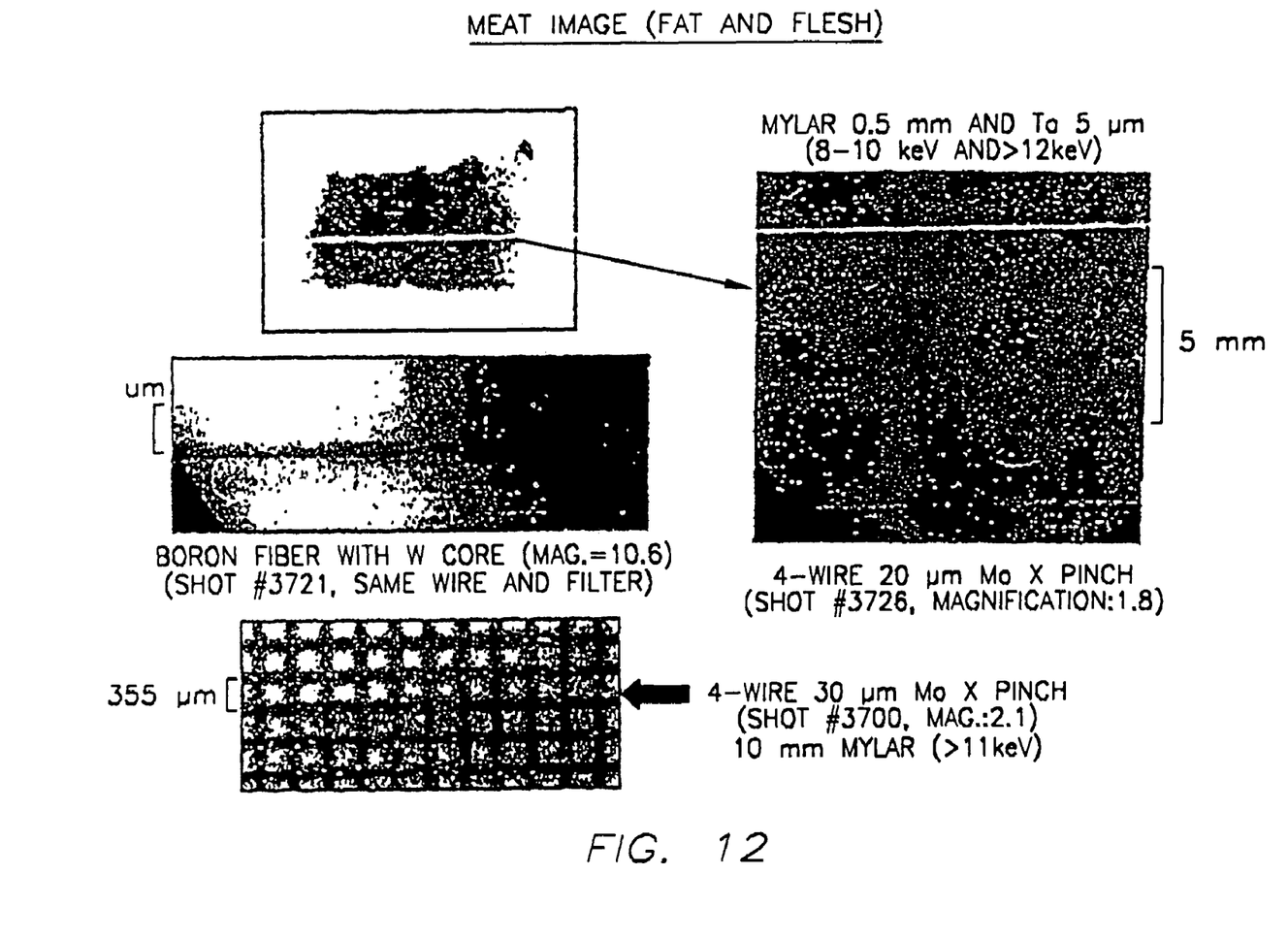

Referring to FIG. 12, there are illustrated a radiographic image of a piece of meat, more particularly from a warm bloodied animal and still more particularly showing the differences between flesh and fat. Both 0.5 mm mylar and 5 µm Ta filters were used for energies in the 8-10 keV range and for energies greater than 12 keV, as illustrated in FIG. 12. A 4-wire 20 µm Mo X pinch was used. An optical photograph of the ~1 mm thick piece of beef is shown in the upper left picture illustrating the combination of muscle and fat tissue in the sample. The radiograph image of a portion of the sample is shown together with a mesh at the top that has a wire spacing of 920 microns and wire size of 90 microns to give a scale. In the lower portion of the image is a straight shadow due to a 100 µm diameter boron fiber with a 17 µm diameter tungsten core showing the resolution.

TABLE 1

X-RAY IMAGING IN X PINCH RADIATION

| | Soft X-ray Type (a) | Intermediate X-ray Type (b) |
|---|---|---|
| Nature Photon Energy (keV) | Thermal 2-5 ~8 | 2-15 |
| Source Size | 1-5 | 2-15 |
| Pulse Duration (ns) | 0.01-0.1 | 0.01-0.1 |
| Yield (J) | 0.01-1.0 | 0.01-1.0 |

The Table entitled "X-RAY IMAGING IN X PINCH RADIATION" summarizes the characteristics of the radiation produced by an X pinch. The radiation up to about 8 keV has a source size consistently under 5 µm and often smaller than 1 µm. The pulse duration is subnanosecond, and the estimated energy from the X pinch in the 2-8 keV energy band is as great as 1 J. Radiation from X pinches with higher currents (and more wires) include energies up to 15-20 keV that come from the same (high temperature thermal) source as the lower energy component and have similar source size.

When filtering cuts off all photons below 15 keV, "contact imaging" (in which the film or detector is immediately behind the object) can be done with photons in the range 20-100 keV, The pulse duration is several nanoseconds, the source size is 50-200 microns and the total energy in the band is up to 10 J on a modest size (500 kA) pulsed current source. This source is not coincident in space with the thermal source, but is located on the anode side of it, as was demonstrated by the slit radiograph shown in FIG. 11. This geometry and source size produces no edge-enhancement but can be used for radiography of thick objects. The only advantage to using an X pinch over other sources in the 20-100 keV range is the short pulse relative to other sources that work well in this range, such as x-ray tubes.

While there has been disclosed what is considered to be the preferred embodiment of the present intention, it is understood that various changes in the details may be made without departing from the spirit, or sacrificing any of the advantages of the present invention.

All publications and patent documents cited in this application are incorporated by reference in their entirety for all purposes to the same extent as if each individual publication or patent document were so individually denoted.

The invention claimed is:

1. A radiograph system comprising an anode plate; a cathode plate; a power source coupled to said anode plate and said cathode plate; at least two wires coupled between said anode plate and said cathode plate providing a configuration to form an X-pinch having a photon source size of less than five microns at energies above 2.5 keV; wherein material at said configuration forming the X-pinch vaporizes upon application of a suitable current to said wires forming a dense hot plasma and emitting a single x-ray pulse with sufficient photons having energies in the range of from about 2.5 keV to about 20 keV; one or more objects in optical communication with the photon source, and one or more x-ray detectors in optical communication with a corresponding object from the one or more objects, whereby each object is positioned between a corresponding x-ray detector from the one or more x-ray detectors and the photon source.

2. The radiograph system of claim 1, wherein at least ten wires provide the configuration forming the X-pinch.

3. The radiograph system of claim 1, wherein the wires are selected from the group consisting of: W, Mo, Ti, Ni, Cr, Pd, Mg, Nb, Al and alloy thereof.

4. The radiograph system of claim 1, wherein the wires are selected from mid- to high-Z materials.

5. The radiograph system of claim 1, wherein the wires are selected from the group consisting of: W, Mo, Nb, Ni and Cr and alloys thereof.

6. The radiograph system of claim 5, wherein the resolution at an object in the path of the photons is better than 5 microns at energies in the range of from 7 to 20 keV.

7. The radiograph system of claim 5, wherein the source size is less than or equal to about 3 microns.

8. The radiograph system of claim 5, wherein the source size is less than or equal to about 1 micron.

9. The radiograph system of claim 5, wherein the resolution at an object in the path of the photons is better than 1 micron at energies in the range of from 7 to 20 keV.

10. The radiograph system of claim 1, and further including one or more fitters between said X-pinch and an object in the path of photons emanating from said X-pinch such that the energies of the photons reaching the object are principally confined to preselected energy values are within about a 2 keV range within the overall range of 7 to 20 keV.

11. The radiograph system of claim 1, wherein photons from said X-pinch radiate in three dimensions simultaneously to pass through a plurality of objects providing a phase contrast image of each object.

12. The radiograph system of claim 1, wherein one or more filters are provided between the X-pinch source of photons and the one or more objects, whereby to select the energies of the photons reaching the one or more object are principally confined to preselected energy values within about a 2 keV range within the overall range of from about 7 keV to about 20 keV.

13. The radiograph system of claim 1, wherein one or more filters are provided between the X-pinch source of photons and the one or more objects and wherein the filters are selected from one or more of several different materials.

14. The radiograph system of claim 1, wherein one or more filters are provided between the X-pinch source of photons and the one or more objects and wherein the filters are made from Ti, Al, Be, Cu, Ta, or combinations thereof.

15. A method providing phase contrast images of an object by subjecting the object to photons having energies in the range of from about 7 keV to about 20 keV, comprising positioning one or more objects around an X-pinch formed by at least two metal wires which, when vaporized and turned into a hot plasma by a current pulse, emit photons having energies in the range of from about 7 keV to about 20 keV from a source spot not greater than about five microns to form a single phase contrast image of each object, by positioning an x-ray detector at a predetermined distance from each object to achieve refraction/diffraction enhancement of the object for a preselected photon energy range, and supplying a high current pulse to the X-pinch to vaporize and ionize the metal wires forming the X pinch x-ray source of photons radiating the objects.

16. The method of claim 15 wherein the source of photons has a size less than one micron at energies above 2.5 keV.

17. The method of claim 15 wherein a plurality of wires provide the configuration forming the X-pinch.

18. The method of claim 15, wherein the resolution at an object in the path of the photons is better than 5 microns at energies in the range of from 7 to 20 keV.

19. The method of claim 15, wherein the resolution at an object in the path of the photons is better than 1 micron at energies in the range of from 7 to 20 keV.

20. The method of claim 15, and further providing one or more filters between the source and the object being radiated to control the energy range of the photons.

* * * * *